United States Patent [19]

Hart et al.

[11] 4,277,131

[45] Jul. 7, 1981

[54] ANTIFOULING WINDOW ASSEMBLY

[75] Inventors: W. Howard Hart, Largo, Fla.; Helmut E. Weber, Valley Forge, Pa.

[73] Assignee: The United States of America as represented by the Administrator of the United States Environmental Protection Agency, Washington, D.C.

[21] Appl. No.: 116,525

[22] Filed: Jan. 29, 1980

[51] Int. Cl.³ .............................................. G02B 7/00
[52] U.S. Cl. ...................................... 350/63; 356/439
[58] Field of Search .................. 350/63; 356/438, 439; 250/573, 574, 575

[56] References Cited

U.S. PATENT DOCUMENTS

| 1,012,403 | 12/1911 | McNeill et al. | 356/438 |
| 1,103,603 | 7/1914 | McNeill et al. | 356/438 |
| 1,135,651 | 4/1915 | Babcock | 356/439 |
| 1,487,898 | 3/1924 | Stolp | 356/438 |
| 2,118,716 | 5/1938 | Wagner | 350/63 |
| 2,374,762 | 5/1945 | McNitt | 356/439 |
| 2,856,542 | 10/1958 | McPheeters | 350/63 |
| 3,170,068 | 2/1965 | Petriw et al. | 250/574 |
| 3,564,272 | 2/1971 | Payton et al. | 356/439 |
| 3,628,028 | 12/1971 | Thorsheim | 250/573 |
| 3,847,487 | 11/1974 | Boll | 356/438 |
| 3,881,112 | 4/1975 | Roberts | 250/575 |
| 4,113,386 | 9/1978 | Lepper | 250/574 |

Primary Examiner—Jon W. Henry

[57] ABSTRACT

An antifouling window assembly in a duct gas monitoring system comprises a mixing chamber positioned between a duct opening and a window unit. Purge gas is introduced into the mixing chamber through an inlet located adjacent the window unit. The velocity of the purge gas is such that laminar flow is established along the surface of the window unit. The purge gas circulates within the chamber and passes into the duct through the duct opening to mix with duct gases and deflect the gases from the mixing chamber.

5 Claims, 6 Drawing Figures

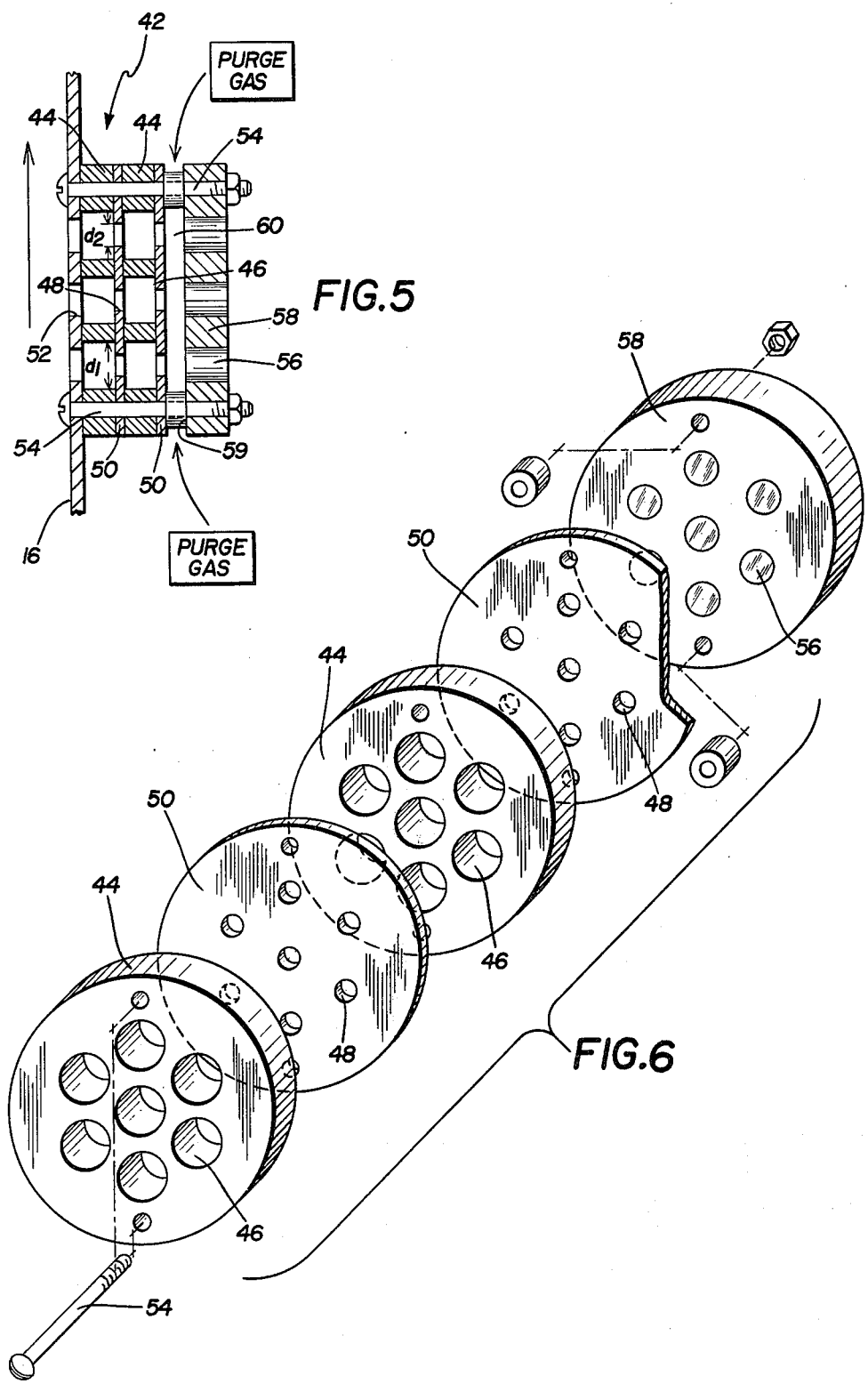

ANTIFOULING WINDOW ASSEMBLY

FIELD OF THE INVENTION

The present invention relates generally to window assemblies for viewing duct gases and more particularly to an antifouling window assembly that reduces purge gas requirements by providing substantially laminar flow of the gas past a window unit and circulating the purge gas within or passing it through a chamber before passing the gas into the duct to mix with and deflect duct gases.

BACKGROUND ART

In the monitoring of oil and coal combustion processes, the gases flowing within a stack or duct into the atmosphere are examined optically for content. The temperature within the duct is within the range of 90° C. to 260° C. with gas velocities up to 18 meters/-second. The duct gases contain acid and water vapors as well as condensation and particulate matter. These conditions made in situ monitoring of the duct gases impractical. In practice, therefore, the duct gases have been monitored using an optical detector mounted on the outer surface of the duct at a duct opening. The detector is exposed to the duct gases at the opening through a window unit that tends to become fouled by the particulate content of the gases. In order to maintain constant the sensitivity of the monitoring system, the windows must be periodically cleaned; cleaning in practice is required following one to four hours of operation.

One system for reducing fouling of the window unit in a duct monitoring system using optical instrumentation involves applying a purge gas to the window to minimize contact of the particulate matter with the window surface. An exemplary system of this type is shown in U.S. Pat. No. 3,847,487 to Boll. Although generally somewhat satisfactory, prior art purge gas systems typically require introduction of a substantial amount of the gas. Because there is a violent movement of the gas in proximity to the window and duct opening, the normal flow of duct gases is significantly altered. The sensitivity of the instrument is reduced because the particulate matter tends to be deflected deeply into the duct out of the field of view of the optical detector.

Another technique for reducing window fouling is to transform the housing on which the window unit is mounted to a number of smaller cylinders having a large length-to-diameter ratio. This technique, used in the conventional "Everclean" window developed by C. E. R. L., is based upon the principal that dust will not be deposited at the end of a cylinder at right angles to the duct if the ratio of the length-to-diameter is at least 4:1 for coarse particles and 16:1 for finer dust and fumes. A disadvantage of the "Everclean" approach, however, is that the large length-to-diameter ratio of the cylinders causes the resulting housing to be excessively long in some applications. An even more serious deficiency is that the long narrow cylinders tend to pass only light parallel to or only slightly diverging from the axes of the cylinders; widely diverging light is blocked from the optical detectors by the cylinder walls.

It is accordingly one object of the present invention to provide a new and improved system for minimizing fouling of duct viewing windows.

Another object is to provide a system for reducing fouling of viewing windows using less purge gas than previously required.

A further object is to provide a new and improved system for reducing fouling of duct gas viewing windows wherein there is minimum interference with flow of duct gases on the viewing axis.

Another object is to provide a new and improved system for minimizing fouling of duct gas viewing windows wherein there is minimum attenuation of light widely diverging from the viewing axis of the window.

An additional object is to provide a purge gas system for reducing fouling of duct gas viewing windows that is more compact tham similar systems of the prior art.

DISCLOSURE OF INVENTION

An antifouling window assembly, in accordance with the invention, comprises a housing defining a mixing chamber located between a window unit and duct opening. An inlet for purge gas is located adjacent the window unit and oriented to inject the purge gas into a chamber forming the interior of the housing at a velocity to cause substantially laminar flow past the surface of the window unit. Because the diameter of the housing is greater than the diameter of the duct opening, and further because the stack gas interacts to drive the exiting purge gas at the duct opening, the purge gas circulates nonviolently within the chamber and in a direction controlled by the stack gas. This circulating purge gas tends to mix with any stack gas entering the chamber and to exhaust the mixed stack gas through the duct opening before the stack gas can migrate to the window unit. In addition, the exiting purge gas is made to flow at a rate that establishes a stable or nearly stable mixing line which projects into the duct. This mixing line or boundary itself deflects stack gas away from the chamber. The injection flow rate of the purge gas is made sufficient to establish a mixing line or boundary at an angle with the wall of the duct of from between 5° and 15°. This acute angle minimizes interference with the duct gases at the viewing axis of the window assembly while also minimizing seepage of the duct gases into the chamber.

In a second embodiment of the invention, the mixing chamber is divided into first and second serial chambers by a dividing plate having a central orifice on the viewing axis of the window assembly. Nonviolent, oppositely directed circulation of duct gases occurs within each of the two series chambers before passing into the duct through the duct opening. The serial effect of the two mixing chambers in the outer chamber substantially reduces window fouling compared to the single chamber embodiment.

In another embodiment, a combination of the "Everclean" and mixing chamber principals is employed to further reduce window fouling while also reducing overall chamber length by abutting together alternately a plurality of first and second orifice plates. The first orifice plates have an array of orifices of a first diameter defining mixing chambers that are positioned in registration with corresponding smaller diameter orifices in the second plates. The two arrays of orifices are further positioned in registration with a window unit or an array of viewing window units located on a supporting disk spaced apart from the outermost orifice plate and with an array of openings formed in the duct to expose the duct gases. Purge gas is supplied nearly tangentially into the assembly adjacent the window unit or the array of window units to be circulated successively within the series mixing chambers before entering the duct through the array of duct openings.

Still other objects and advantages of the present invention will become readily apparent to those skilled in this art from the following detailed description, wherein we have shown and described only the preferred embodiments of the invention, simply by way of illustration of the best modes contemplated by us of carrying out our invention. As will be realized, the invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF DRAWINGS

FIG. 5 is a diagrammatic cross sectional side view showing incorporation of first and second types of orifice plates into the mixing chamber to reduce chamber length and further reduce window fouling in accordance with a third embodiment of the invention; and FIG. 6 is a exploded view of the assembly shown in FIG. 5.

BEST MODE FOR CARRYING OUT THE INVENTION

Figure 1:
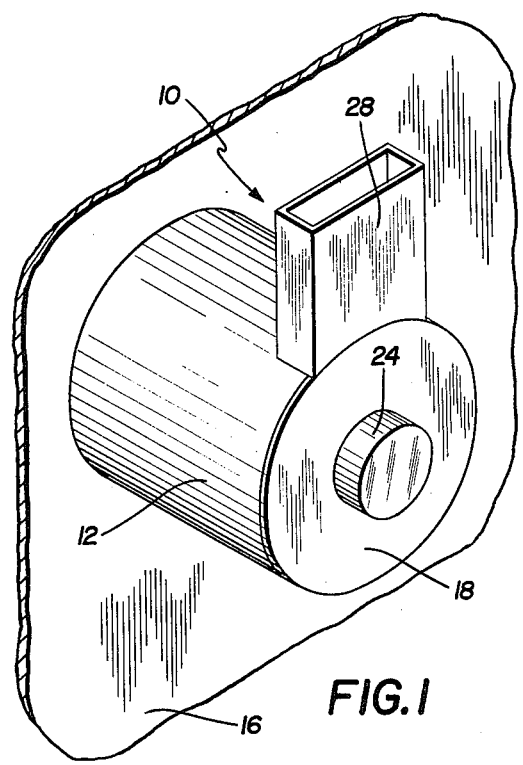
FIG. 1 is a perspective view of an antifouling window assembly according to the principles of the present invention.
Figure 2:
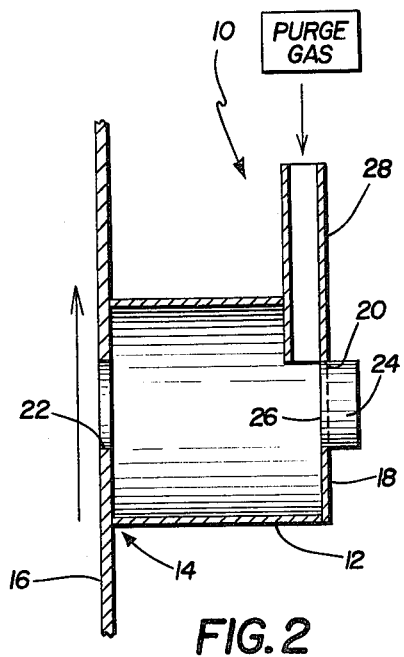
FIG. 2 is a cross sectional side view of the assembly shown in FIG. 1.

Referring to FIGS. 1 and 2, an antifouling window assembly 10 comprises a cylindrical housing 12 having an open end 14 mounted to the wall of a duct 16 through which are flowing hot gases to be viewed by monitoring instrumentation (not shown). At the opposite end 16 of the housing 12 is a cap 18 having a central orifice 20 located on a common axis with a corresponding opening 22 formed in the duct 16. The diameter of housing 12 is approximately twice the diameter of duct opening 22. A window unit or lens 24 is positioned within the orifice 20 of end cap 18 and has an inner surface 26 that is flush with inner surface 28 of the end cap 18.

An inlet 28 for purge gas, such as clean air, is positioned radially into the housing 12 at end 16. The inlet 28 is oriented on housing 12 to inject the purge gas into chamber 30 within the housing at a direction opposite the flow direction of the duct gases. As shown in FIG. 1, the inlet 28 has a rectangular cross section and extends outwardly from the housing by a substantial distance. The length of the inlet 18 is such that it abuts the curved surface of window unit 24 and is oriented parallel to the inner surface 26 of the unit.

Figure 3:
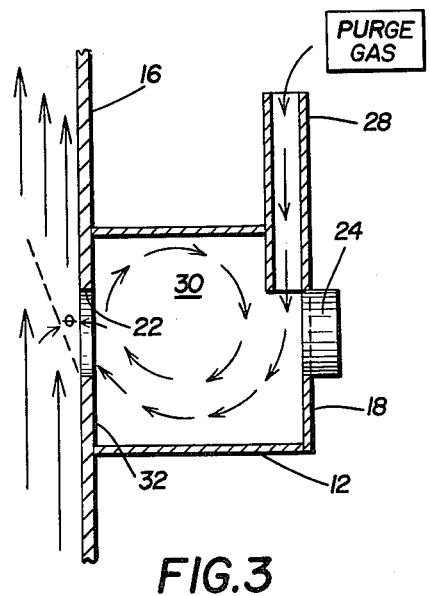
FIG. 3 is a diagrammatic view corresponding to FIG. 2 showing flow direction of stack gases and purge gas.

Referring to FIG. 3, stack gases flow upwardly within the duct 16 and are exposed through duct opening 22 to the window unit 24 through chamber 30 within the housing 12. The purge gas is introduced into inlet 28 in the direction of the arrow (opposite the flow direction of the stack gases) at a velocity to establish substantially laminar flow past the inner surface 26 of the window unit 24 as shown. The purge gas is caused to flow in a circular path toward duct opening 22 by interaction through duct opening 22 with the upwardly flowing duct gases. Since the cross sectional area of the chamber 30 is greater than the cross sectional area of the duct opening 22, and since the flow directions of purge gas and stack gases are as shown in FIG. 3, the purge gas is drawn upwardly along duct surface 32 to circulate within the chamber before entering the duct 16 through opening 22.

Mixing of the purge gas and duct gases within the duct 16 occurs across the boundary shown in dotted line. The mixing boundary is oriented at an angle $\theta$ relative to the wall of duct 16 depending upon the velocity and quantity of purge gas injected into the chamber 30. Optimum antifouling of window unit 24 occurs at a purge gas flow velocity that produces a mixing line (separating stream line) angle $\theta$ of between 5° and 15°. This range of boundary angles is obtained by making the available velocity of purge gas through the duct opening equal to a fraction of the stack velocity according to the formula:

$$V_{P_{avg.}} = \tfrac{1}{2} V_S \tan \theta$$

where $V_{P_{avg.}}$ is the average purge gas velocity; and $V_S$ is the stack gas velocity.

For an angle $\theta$ of 5°, the average purge volocity is 0.05 that of the stack velocity; and for an angle $\theta$ of 15°, the average purge velocity is 0.14 that of the stack velocity. These limiting velocities and the area of the duct opening 22 determine the available flow rate for the purge gas.

The purge gas entering duct 16 also deflects the stack gases away from chamber 30. Any stack gases that do enter the chamber 30 as a result of turbulence are diluted and are maintained in motion away from window unit 24 by clean purge gas circulating within the chamber. Any small quantity of stack gases that does reach the inner surface 26 of the window unit 24 tends to be removed by the substantially laminar flow of purge gas egressing from inlet 28. Of course, some stack gas inevitably settles on the window unit surface 26 and is not removed by the purge gas. In practice, however, the structure shown in FIG. 3 increases periods between shut down for cleaning from just a few hours of operation to at least 20-40 hours.

Figure 4:
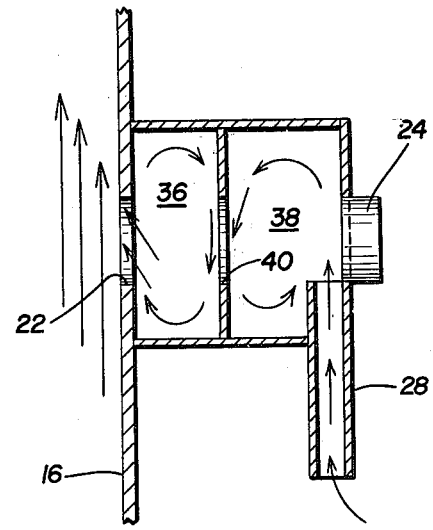
FIG. 4 is a diagrammatic cross sectional side view showing the introduction of an orifice plate for dividing the mixing chamber into first and second serial mixing chambers in accordance with a second embodiment of the invention.

Referring to FIG. 4, a second embodiment of the invention is shown wherein a divider plate 34 is positioned within the chamber 30 to divide the chamber into two approximately equal volume serial chambers 36 and 38. The divider plate 34 has a central orifice 40 that is on a common viewing axis with duct opening 22 and the window unit 24. Inlet 28 is positioned on housing 12 to inject purge gas in a common direction with the flow of duct gas. As shown by the arrows in FIG. 4, divider plate 34 causes successive opposite direction circulations of purge gas in the two serial chambers 36 and 38 before entering the duct 16 through opening 22 to mix with the duct gases. Experimentation has shown that the provision of divider plate 34 within chamber 30 substantially reduces the rate of window fouling by nearly a factor of 10 over that in the embodiment shown in FIG. 3. This is attributed to a "serial effect", wherein the first chamber reduces fouling between the duct opening 22 and the central orifice 40, and the second chamber reduces fouling between the central orifice 40 and the window unit 42.

Referring to FIGS. 5 and 6, a third embodiment of the invention is shown wherein the principles of the "Everclean" window and serial mixing chamber are combined in a single assembly identified generally by the numeral 42. The assembly 42 comprises a plurality of first disks 44 (see also FIG. 6) having an array of orifices 46 of diameter $d_1$. The first disks 44 are in abutment with a plurality of second disks 50 having a corresponding array of orifices 48 of effective diameter $d_2 < d_1$ in registration with the orifices 46 of disks 44. The orifices 46 form a series of small mixing chambers corresponding to chambers 36 and 38 in FIG. 4 whereas the orifices 48 in disks 50 form intermediate openings corresponding to orifice 40 in FIG. 4 between adjacent chambers 46 on a common viewing axis.

Also located on common viewing axes are openings 52 formed in the duct 16 through which duct gases are exposed. The disks 44 and 50 are maintained together in abutment with each other and mounted to the duct 16 by screws 54.

An array of window units 56 is carried by a disk shaped member 58 that is mounted to screws 54 and offset from outer disk 50 by spacers 59. The space between member 58 and outer disk 50 defines a circumferential inlet 60 through which purge gas is introduced into the assembly 42. The purge gas is introduced through the inlet at a velocity to cause substantially laminar flow of gas over the inner surface 62 of the window units 56. If desired, a single inlet or multiple discrete inlets could be provided in place of the circumferential inlet shown in FIG. 5. The purge gas successively circulates within each mixing chamber 46 through intermediate openings 48 in the manner shown in FIG. 4 before mixing with duct gases through duct openings 52. Because each chamber of the "chamber series" formed by chambers 46 and intermediate openings 48 along each viewing axis has a high length-to-diameter ratio, there is further isolation of the window units from duct gases based on the "Everclean" principal, supra, to minimize fouling.

In this disclosure, there is shown and described only the preferred embodiments of the invention, but, as aforementioned, it is to be understood that the invention is capable of use in various other combinations and environments and is capable of changes or modifications within the scope of the inventive concept as expressed herein.

We claim:

1. In a duct gas monitoring system including window means for viewing duct gases through a duct opening, wherein there is a tendency for the window means to become fouled by particulate matter in said gases, an antifouling window assembly comprising a housing having an open end mounted on said duct at the duct opening, said housing having a cross sectional area greater than the cross sectional area of said duct opening and defining a circulation chamber means; inlet means for supplying a purge gas into said housing at a flow velocity to provide substantially laminar gas flow along a surface of said window means, said housing including a divider plate for dividing said chamber means into a first chamber adjacent said window means and a second chamber adjacent said duct opening, said divider plate containing an an orifice located on a viewing axis, said purge gase circulating successively within said first and second chambers before passing into said duct through the duct opening to mix with the duct gases.

2. The window assembly of claim 1, wherein the duct opening and the divider plate orifice have a common diameter, the length of each of said chambers of said housing being equal approximately to said common diameter.

3. The window assembly of claim 1, wherein said duct contains an array of duct openings; said window means including a corresponding array of window units; a plurality of first and second orifice plates abutting each other and alternately disposed within said housing, said first plates containing an array of first orifices defining mixing chambers; said second plates containing a corresponding array of second orifices defining intermediate orifices; said first and second plate orifices being in registration with said duct openings, with said window units and with each other; said purge gas sucessively circulating within said chambers and intermediate orifices before passing into said duct through said duct openings.

4. The window assembly of claim 3, wherein said window units are mounted in a disk, said disk being offset from said housing to provide a cicumferential purge gas supply inlet.

5. The window assembly of claim 1, wherein said window means includes a window unit coplanar with an inner end wall surface of said housing.

* * * * *